United States Patent [19]
Hassler et al.

[11] Patent Number: 5,330,502
[45] Date of Patent: Jul. 19, 1994

[54] ROTATIONAL ENDOSCOPIC MECHANISM WITH JOINTED DRIVE MECHANISM

[75] Inventors: William L. Hassler, Sharonville; Thomas Murray; Charles Armstrong, both of Cincinnati; Daniel Price, Loveland, all of Ohio

[73] Assignee: Ethicon, Inc., Somerville, N.J.

[21] Appl. No.: 959,017

[22] Filed: Oct. 9, 1992

[51] Int. Cl.$^5$ .............................................. A61B 17/00
[52] U.S. Cl. .................................. 606/205; 606/170; 606/174; 128/751
[58] Field of Search ...................... 606/51, 52, 83, 174, 606/205-211; 128/750-755

[56] References Cited

U.S. PATENT DOCUMENTS

| | | | |
|---|---|---|---|
| 4,674,501 | 6/1987 | Greenberg | 606/174 |
| 4,763,669 | 8/1988 | Jaeger | 606/174 |
| 4,872,456 | 10/1989 | Hasson . | |
| 4,880,015 | 11/1989 | Nierman | 128/751 |
| 4,944,741 | 7/1990 | Hasson | 606/207 |
| 5,133,735 | 7/1992 | Slater et al. . | |
| 5,133,736 | 7/1992 | Bales et al. . | |
| 5,141,519 | 8/1992 | Smith et al. . | |
| 5,152,778 | 10/1992 | Bales et al. . | |
| 5,156,633 | 10/1992 | Smith . | |
| 5,174,300 | 12/1992 | Bales et al. . | |
| 5,209,747 | 5/1993 | Knoepfler | 606/52 |

FOREIGN PATENT DOCUMENTS 3447769  7/1986  Fed. Rep. of Germany ...... 606/208

*Primary Examiner*—Michael H. Thaler
*Assistant Examiner*—William W. Lewis
*Attorney, Agent, or Firm*—Paul A. Coletti

[57] ABSTRACT

Described herein is an endoscopic instrument such as a dissector, scissor or grasper in which there is provided a shaft which defines a longitudinal axis of the instrument. This shaft is able to rotate about the handle portion of the instrument. This mechanism also provides for articulation of the end effectors with respect to the longitudinal axis of the shaft. This articulation is accomplished by causing angulation of the end effector with respect to the shaft. Because driving the cable is accomplished around any such angle, the end effectors continue to be able to operate. There is disclosed herein a locking mechanism which allows the rotational aspect of the device to operate to rotate the entire articulating mechanism.

15 Claims, 5 Drawing Sheets

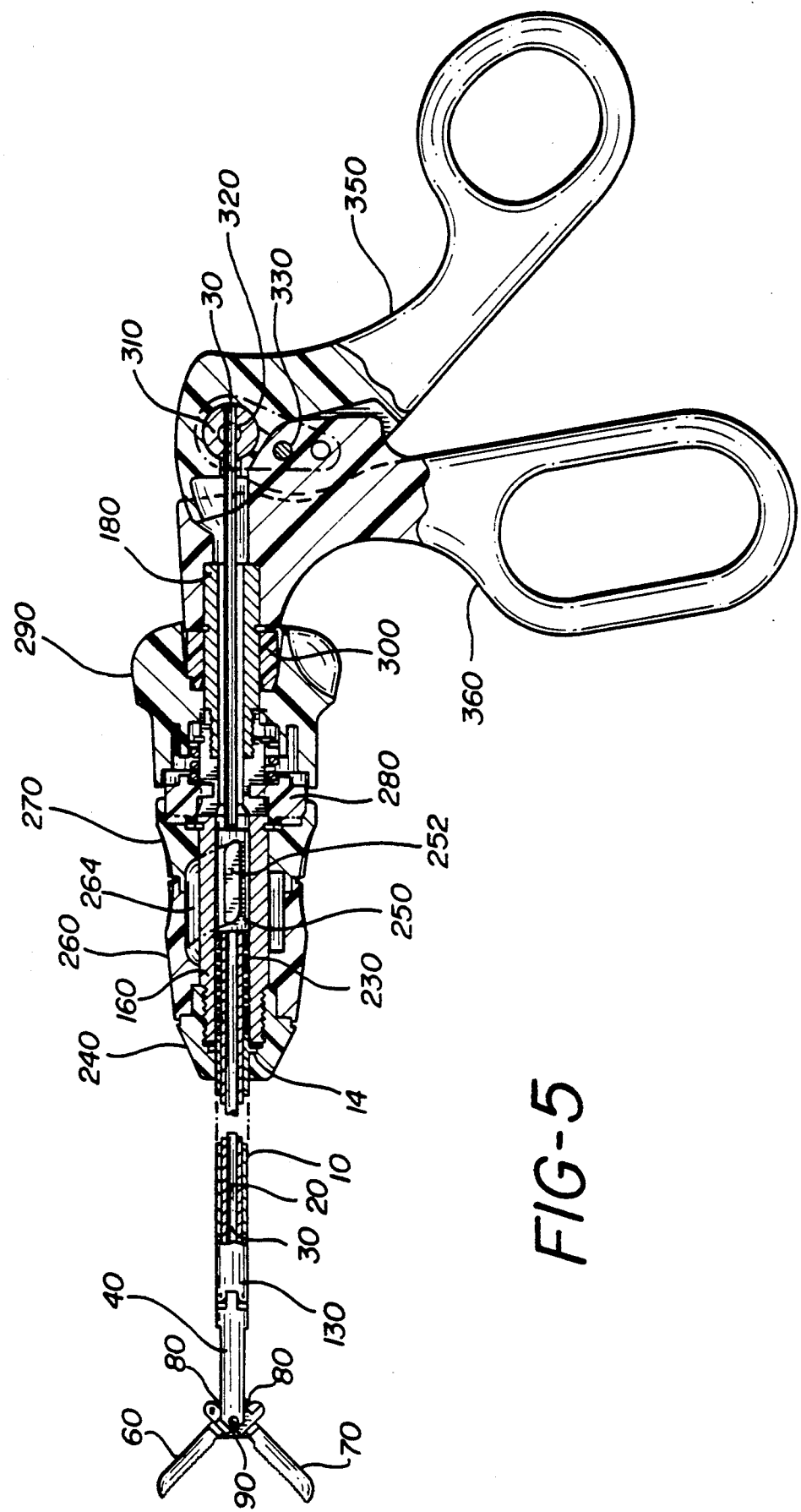

ROTATIONAL ENDOSCOPIC MECHANISM WITH JOINTED DRIVE MECHANISM

FIELD OF THE INVENTION

Generally, this invention relates to endoscopic mechanisms. More specifically, this invention relates to endoscopic mechanisms such as graspers, dissectors, and scissors, wherein the device is capable of rotating. Most specifically, this invention relates to such mechanisms wherein while the device may rotate around the longitudinal axis of the instrument, the end portion of the shaft is also able to angulate through an articulation, such that the shaft may move from 0° to a 90° angle with the shaft.

BACKGROUND OF THE INVENTION

Within endoscopic surgery, there is a recognized need for simple devices such as graspers, dissectors, scissors, and other basic surgical instruments. These instruments are necessary in order to perform simple functions during the endoscopic procedure. Specifically, devices such as graspers are necessary in order to properly move the work site away from the other vital organs so that the tissue to be worked on may be isolated and surgery may be performed. Scissors may be needed in order to make an appropriate cut in tissue, muscle or other vasculature. Dissectors can be necessary to separate one portion of tissue from another. These instruments also enable the other, larger instruments such as staplers and ligating clip appliers to have enough volumetric room in order to perform operations such as appendectomies, cholecystectomies, herniorrhaphies, etc.

Traditionally, instruments such as graspers, dissectors, scissors and other endoscopic instruments have been mounted on generally straight shafts. These shafts may or may not have been able to rotate about the longitudinal axis of the shaft. Nonetheless, there has been perceived a need for the end effector of the shaft to be able to angulate with respect to the longitudinal axis of the shaft. This may enable the surgeon to attack the tissue which is to be operated from an oblique angle. In fact, it may be desirable to have the shaft angulate up to 90° with respect to the longitudinal axis of the shaft. In many ways, this function can be analogized to the capability of the human hand to rotate around the "axis" of the arm, and also "angulate" about the wrist. Of course, while the hand is able to function with pure rotation, the degrees of freedom given by wrist action are much greater and in many ways enhance the ability of the hand to perform simple daily functions. Thus, there is perceived a need for an articulating, angulating endoscopic instrument so that the functions of such mechanisms can be made much more versatile.

Previously, there have been attempts at creating articulating instruments, but none of these instruments have the capability of performing functions at an angulation of 90° to the longitudinal shaft of the endoscopic mechanism. This is due, in large part, to the tolerancing and material strength problems encountered by the manufacturers of such instruments. It must be remembered that it is necessary to not only have an instrument which can create such angulations, but it also be capable of operating the end effectors at such angulations. This combination has been difficult to create, and has caused design sacrifices to be made. Generally, these sacrifices have been made to the versatility of such instruments, so that such endoscopic instruments are not capable of being angulated at 90° to the shaft of the instrument. Of course, with this restrictive limitation, the ultimate capabilities of such angulations are not met.

SUMMARY OF THE INVENTION

Described herein is an endoscopic instrument such as a dissector, scissor or grasper in which there is provided a shaft which defines a longitudinal axis of the instrument. This shaft is able to rotate about the handle portion of the instrument. Such rotation also causes rotation of the end effectors, such as the scissors and graspers placed at the end of the instrument. Such rotation is effected by a rotating knob placed toward the handle portion of the instrument. The operation of the instrument in order to accomplish grasping and cutting and the like is accomplished by the scissor-like motion of a pair of handles located at the rear of the instrument. One handle is fixed relative to the drive shaft. The other handle is capable of pivoting with respect to the longitudinal axis of the shaft. This rotation causes a sliding motion of a drive shaft contained within the outer tube of the mechanism. The sliding motion of such drive portion is able to operate a flexible cable. This flexible drive cable moves with relation to a clevis, which causes operation of the end effectors contained in such a mechanism. In this way, operation of the mechanism is accomplished, allowing the surgeon to maintain a stationary hand position.

Importantly, this mechanism also provides for articulation of the end effectors with respect to the longitudinal axis of the shaft. This articulation is accomplished by causing angulation of the end effector with respect to the shaft. Articulation is generated by use of a articulating knob which causes a helical screw to exert a relative motion on a winged nut attached to an articulation tube contained in the mechanism. With motion of this drive screw, the articulation tube is caused to move with respect to both the outer tube of the mechanism and the drive shaft. By causing this relative motion, the articulation tube causes a hinged joint to move relative to the outer tube of the mechanism. This joint causes the end effector to angulate with respect to the longitudinal axis of the outer tube. Depending upon the amount of articulation created by the articulation knob, the outer shaft will angulate from 0° to 90° with respect to the outer shaft of the mechanism.

Naturally, once the mechanism has articulated, it is important that the device continue to be able to operate. This is accomplished by a cable-type mechanism which is capable of operating the shaft and its end effectors around the angle created by the articulated angulation. Because driving the cable is accomplished around any such angle, the end effectors continue to be able to operate. In this way, use of the device can be made at any angle between 0° and 90° with respect to the longitudinal axis of the shaft.

Finally, there is disclosed herein a locking mechanism which allows the rotational aspect of the device to operate to rotate the entire articulating mechanism. In this way, during rotational motion, articulation is locked in place, and there is no articulation of the end effector with respect to the longitudinal axis of the shaft. In contrast, during articulation, the rotational mechanism is locked in place so that relative rotational position is maintained. This "clutch"-type mechanism allows the user to accomplish many varied functions during an endoscopic procedure. Utility is maintained, and the enhancements created by this articulated angulation continue to be realized.

This new invention will be better understood in relation to the attached drawings taken in conjunction with the detailed description of the invention.

DETAILED DESCRIPTION OF THE DRAWINGS

FIG. 5 is a cross-sectional view of the handle portion of the instrument of this invention taken across lines 5—5 of FIG. 1.

DETAILED DESCRIPTION OF THE INVENTION

Figure 1:
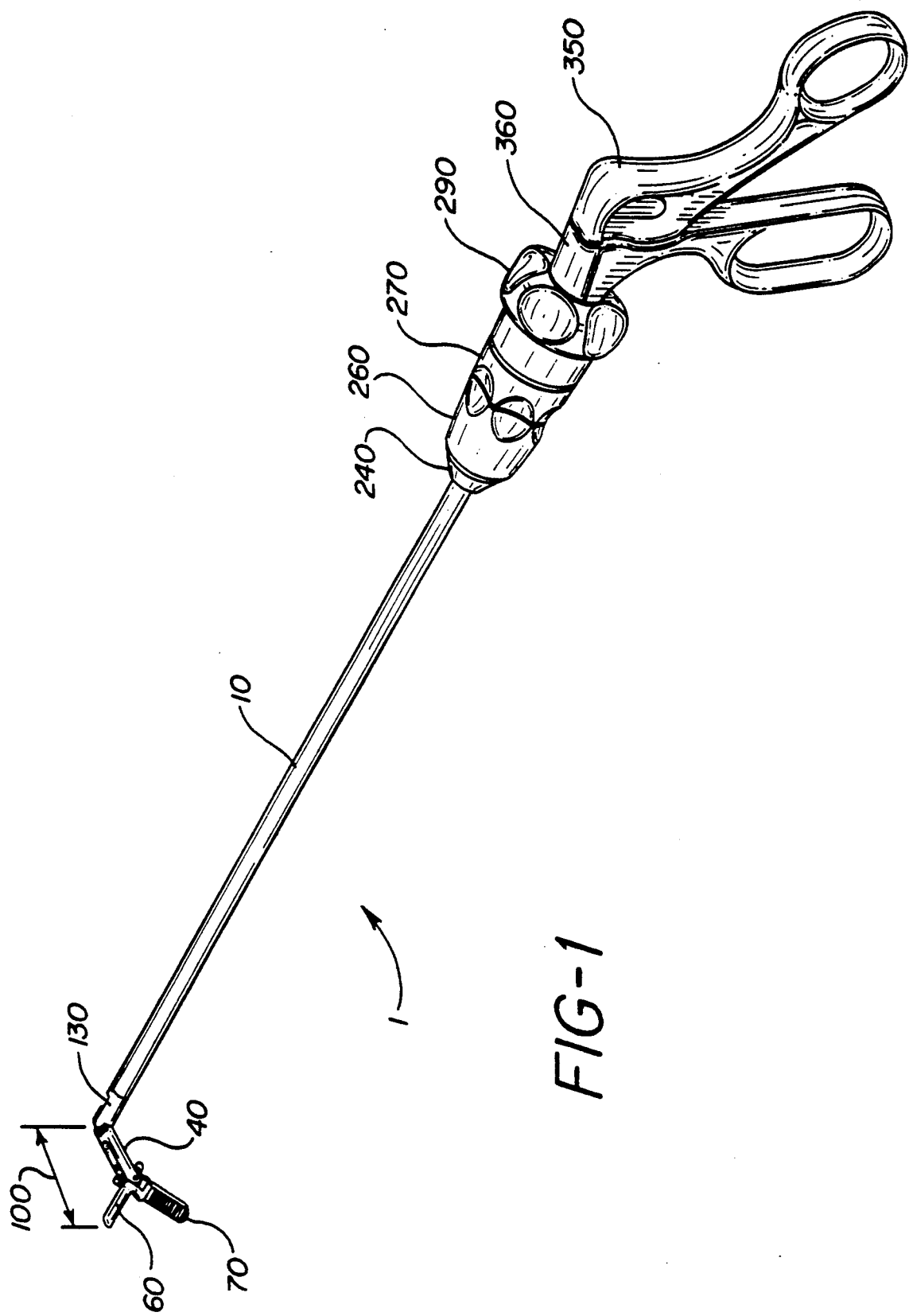
FIG. 1 is a perspective view of an endoscopic instrument of this invention.

A device 1 for performing endoscopic procedures is described herein, and is seen generally in FIG. 1. This device 1 is capable of rotating about the shaft or outer tube 10 of the mechanism. As well, this device 1 is capable of being angulated so that the end effector portion 100 of the mechanism may be placed at an angle up to 90° with respect to the longitudinal axis formed by the shaft of the mechanism, as better seen in FIG. 4. Each of these functions will be described herein.

Figure 2:
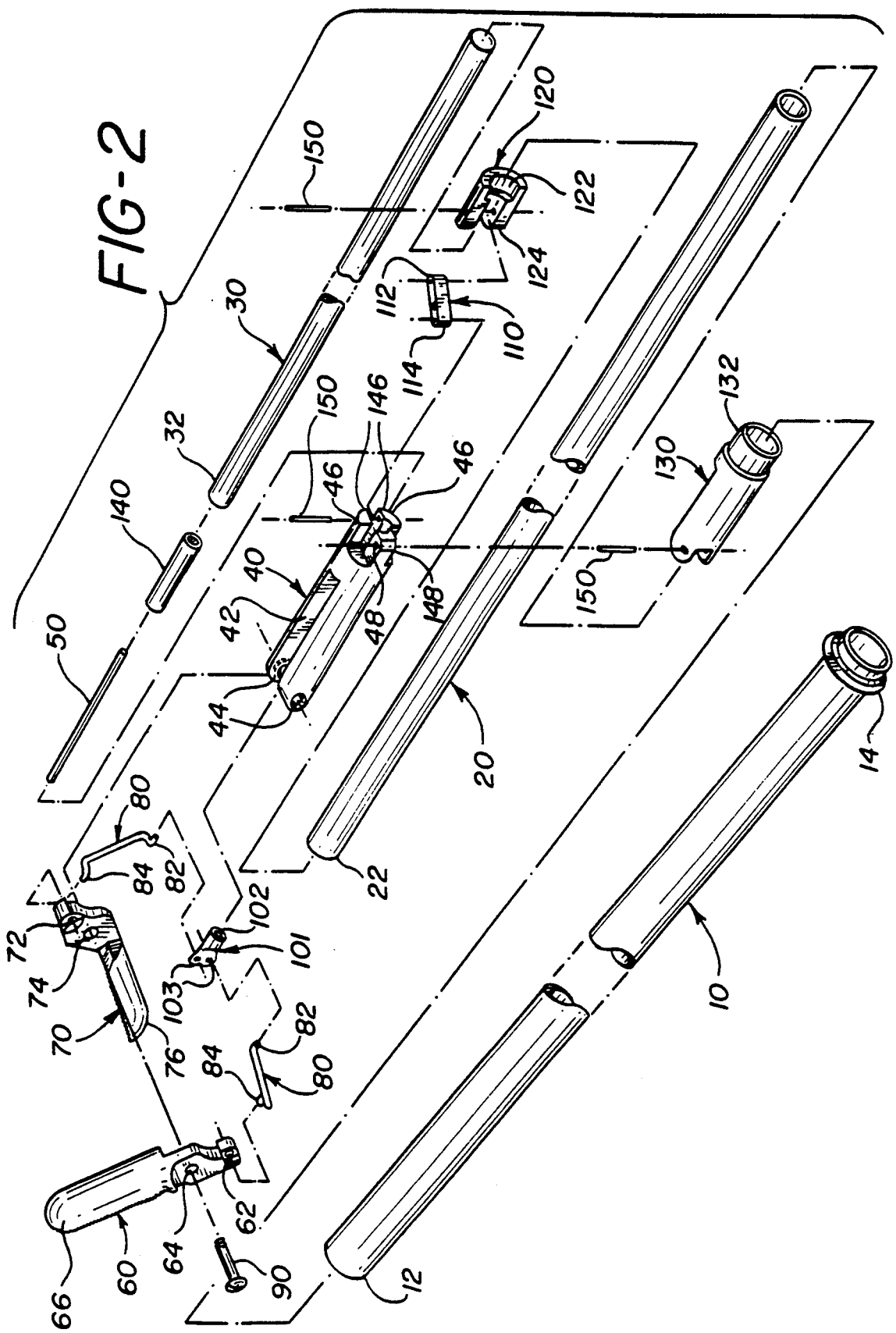
FIG. 2 is a exploded assembly view of the end effector portion of the instrument of this invention.

As better seen in FIG. 2, there is described a drive rod 30 which is generally cylindrical and runs for the entire length of the instrument. This drive rod 30 is capable of being placed within an articulation tube 20. The articulation tube 20 is also cylindrical and is able to be moved longitudinally with respect to the drive rod 30. Further, the articulation tube 20 and the drive rod 30 fit within the outer tube 10 of the mechanism.

The driving portion of the mechanism and its end effectors will now be described. The drive rod 20, as has been previously explained, is capable of moving in a sliding direction with respect to the outer tube 10. This drive rod 30 is connected to a drive cable 50 at crimp 32 at the distal end of the drive rod 30. This drive cable 50 fits securely within a cable sleeve 140. At the distal portion of the drive cable 50, there is attached a rod end 101 at crimp 102. This rod end 101 is capable of generating the functions of the particular mechanism. The rod end 101 is held within the longitudinal center 42 of clevis 40. The drive cable 50 also fits securely within the center 42 of the clevis 40 and both the rod end 101 and drive cable 50 are capable of moving with respect to the clevis 40.

When the drive cable 50 is moved with respect to the clevis 40, it guides the rod end 101 in a longitudinal fashion with respect to the clevis 40. In so doing, the rod end 101 is capable of pivoting the pair of jaw links 80. These jaw links 80 rotate about the rod end 101 at pivot points 103 connected to flared ends 82 so that jaw links 80 flare outwardly from the axis created by the drive rod 30 and the drive cable 50.

At the distal end of the rod links 80, are attached the end effectors of the instrument. For instance, in this example, there are shown end effectors which comprise upper jaw 60 and lower jaw 70 of a grasping mechanism. However, it is to be understood that these end effectors may be scissors or dissectors or other endoscopic instruments. What is necessary is that the end effectors 60, 70 are attached at their respective proximal end 62,72 to the distal ends 84 of the jaw links 80, in order that the jaw links 80 may guide motion of the end effectors 60, 70.

Thus, when the drive rod 30 is moved in a proximal fashion toward the user, the drive cable 50 is similarly pulled in a proximal direction. This drive cable 50 is capable of pulling the rod end 101 so that it to moves in a proximal direction. Because the jaw links 80 are connected to the rod end 101 at the pair of pivoting points 103, the jaw links 80 are similarly pulled in a proximal direction. In this manner, the jaw links 80 rotate from an outwardly flared position to an inwardly flared position with respect to the longitudinal axis of the drive rod 30. When this occurs, the jaw links 80 at their distal ends rotate the proximal ends of the end effectors 60, 70 toward the longitudinal axis of the instrument. The end effectors 60, 70 are pivoted at points 64,74 about shoulder screw 90 attached to pivot holes 44 contained at the end of the clevis 40. Thus, the end effectors 60, 70 similarly rotate about the clevis 40 so that the entire mechanism is "closed".

On the other hand, when the drive rod 30 is pushed distally, the rod end 101 causes the jaw links 80 to flare outwardly from the longitudinal axis of the drive rod 30. This outward flaring causes the ends 66, 76 of the end effectors 60, 70 to similarly move outwardly. The end effectors 60, 70 pivot at points 64, 74 about shoulder screw 90 connected to the pivot holes 44 at the end of clevis 40. Thus, with this rotation, the end effectors 60, 70 also pivot so that the device is now "open". In this fashion, therefore, reciprocal motion of drive rod 30 operates the jaws 60, 70 of the mechanism 1.

It is to be understood that the drive rod 30 is capable of moving with respect to both the articulation tube 20 and the outer tube 10 of the mechanism 1. In this fashion, motion of the drive rod 30 is capable of being performed regardless of the relative positioning of either the articulation tube 20 or the outer tube 10. Thus, the motion of the drive rod 30 is capable of causing performance of the end effectors 60, 70 at any rotational position of the mechanism 1.

There is further described at the distal or end effector portion 100 of the mechanism 1 an articulation function. This articulation is understood from observing motion of the articulation tube 20 in relation to the outer tube 10 of the mechanism. The articulation tube 20 is connected by a weld at its distal end 22 to the internal chamber 122 of slider elbow 120. The outer tube 10 is rigidly connected at its distal end 12 so that it fits over the smaller outer circumference 132 contained at the proximal end of fixed elbow 130. The slider elbow 120, therefore, is able to move with respect to the outer tube 10 along the longitudinal axis of the mechanism 1. (This can be better seen in FIGS. 1 and 4, for instance. There, the articulation tube 30 has moved distally. Similarly, the slider elbow 120 has been moved distally by the articulation tube 20. This sliding motion causes the angulation of the end effectors portion 100 of the mechanism, and will be further described herein.)

The distal end 124 of the slider elbow 120 is connected by a pin 150 to the proximal end 112 of the elbow link 110. This elbow link 110 is connected by a similar pin 150 at its opposite or distal end 114 to pivot holes 46 on tabs 146 of clevis 40. Similarly, the clevis 40 is connected by pin 150 at pivot hole 48 on an opposite tab 148 to the fixed elbow 130. With these connections arranged in this fashion, angulation of end effector portion 100 about the longitudinal axis of the instrument can be accomplished. Thus, when the articulation tube 20 is moved distally, the slider elbow 120 is also moved distally. This distal movement of the slider elbow 120 causes rotation of the elbow link 110 about the proximal end 112 connected to slider elbow 120. Such motion similarly causes motion of the elbow link 110 about distal end 114 connecting elbow link 110 and clevis 40. However, because the clevis 40 is fixed at tab 148 to the fixed elbow 130 connected to longitudinal axis of outer tube 10, the clevis 40 is caused to rotate about the longitudinal axis of outer tube 10, in the manner of a typical four-bar linkage.

Figure 4:
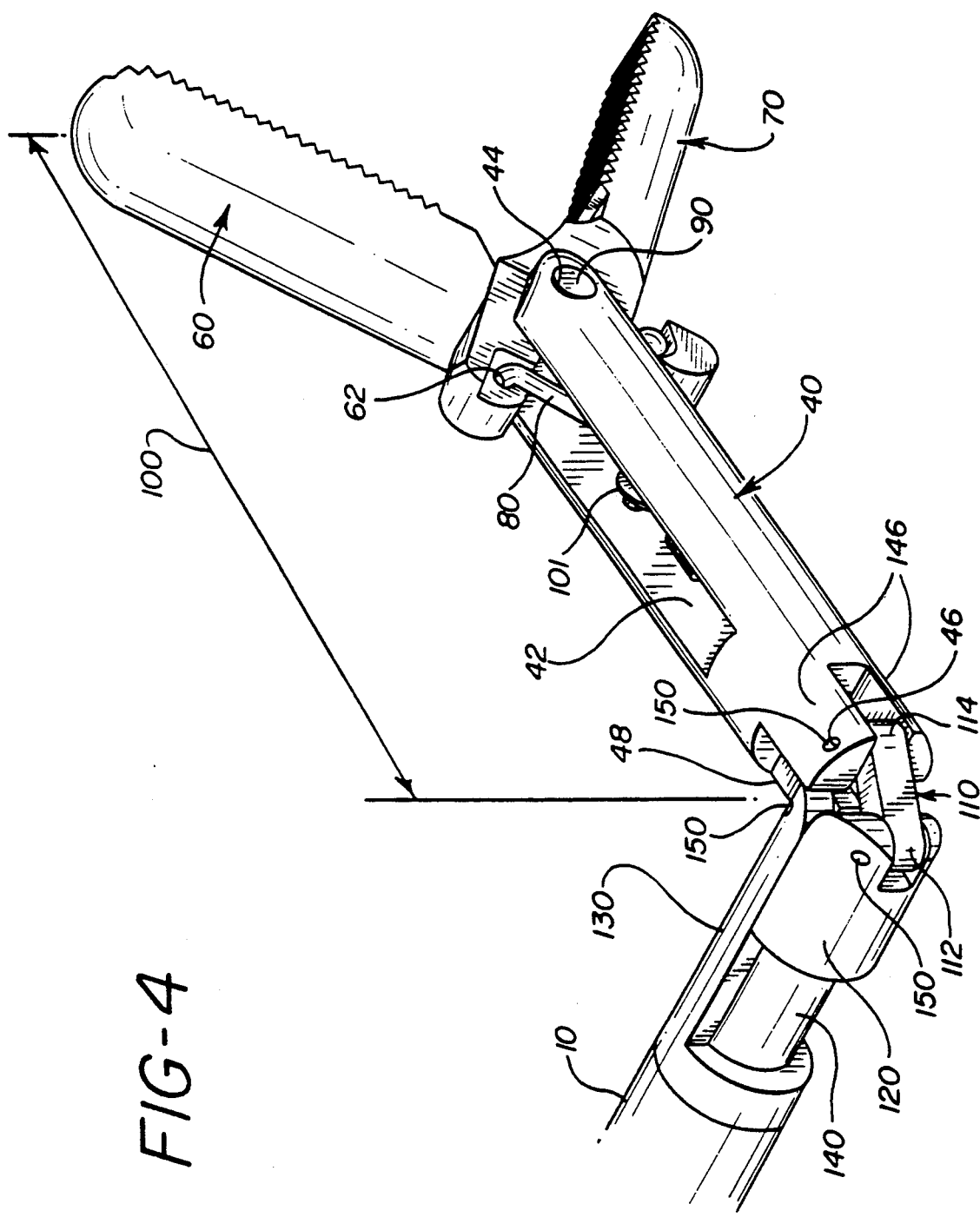
FIG. 4 is a perspective view of the articulated end of the instrument of this invention.

This can be best be seen in FIG. 4, where motion has been accomplished. There, it is seen that the distal motion of the slider elbow 120 has caused angulation of the clevis 40 about the outer tube 10. Of course, proximal motion of the slider elbow 120 caused by proximal motion of the articulation tube 20 causes return rotation of the clevis 40 to a position where there is no angulation between the clevis 40 and longitudinal axis of the outer tube 10.

It is mutually desirable to accomplish operation of this mechanism at any angulation of the clevis 40 with respect to the outer tube 10. Thus, it is important for the drive rod 30 to be able to move with respect to the clevis 40 with any angular position of the clevis 40. This is accomplished through use of the attachment of drive rod 30 to the drive cable 50. Because the drive cable 50 is flexible, it can move along with the angular positioning of the clevis 40 in relation to the position of the outer tube 10, the articulation tube 20 and the drive rod 30. The drive cable 50 is contained in cable sleeve 140 made from a low friction material such as Teflon™, and therefore motion of the drive cable 50 within the clevis 40 is readily accomplished.

Thus, motion of the drive cable 50 can be accomplished at any angular position of the clevis 40 with respect to the outer tube 10, even at 90° angles, which has heretofore not been possible for any articulating type endoscopic instruments.

Figure 3:
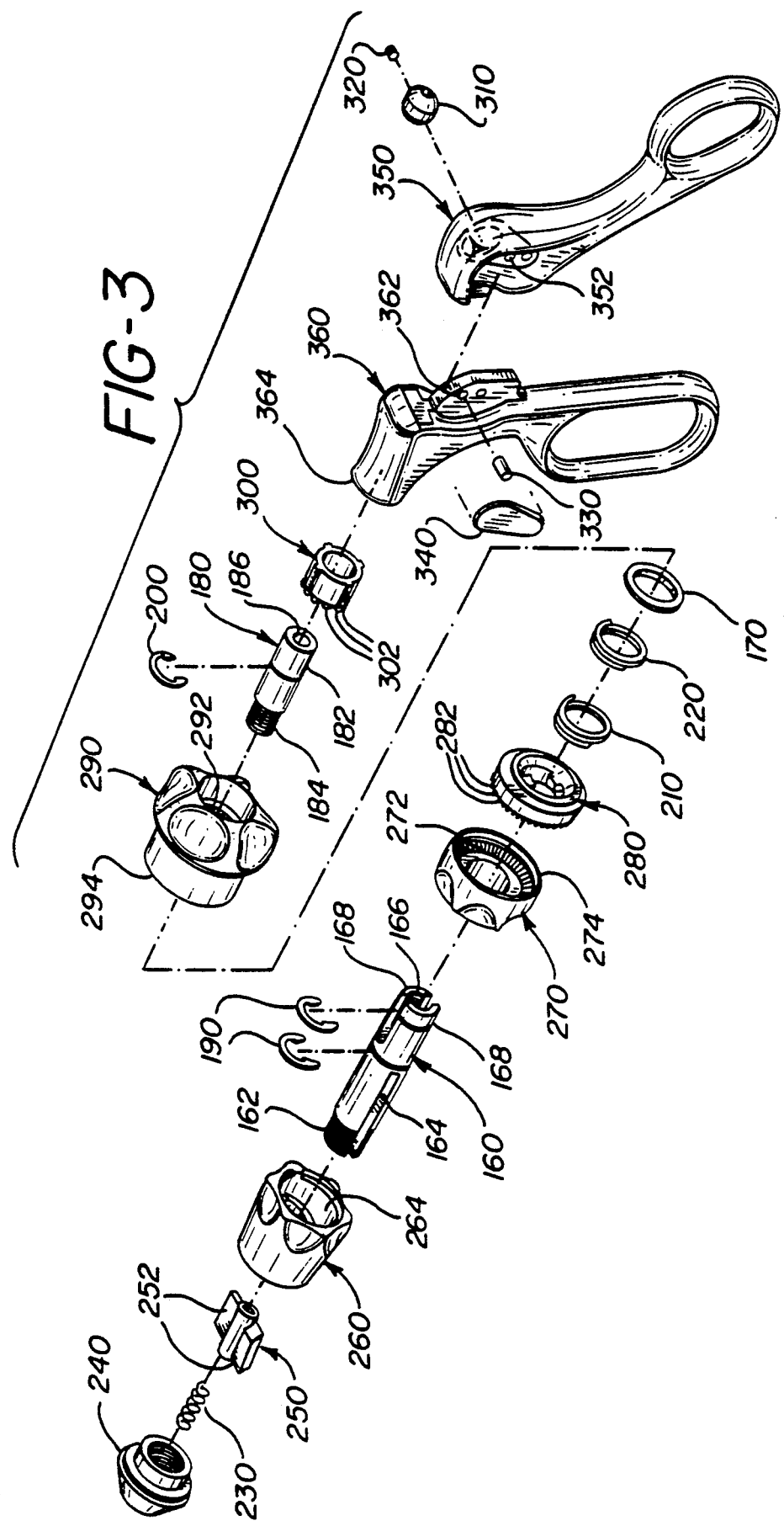
FIG. 3 is an exploded assembly view of the handle portion of the present invention.

Now that the end effector 100 portion of the mechanism has been described, this mechanism 1 must be understood in conjunction with the control portion of the instrument contained in its handle. It must be remembered that while articulation and operation of the end effectors 60, 70 are accomplished, only three portions extend into the handle. That is, only the outer tube 10, the articulation tube 20, and the drive rod 30 extend into the handle section of the instrument. Importantly, it is to be noted that the outer tube is connected via its flange 14 to the end cap 240 of the front piece of articulation knob 260 of the instrument. This can best be seen in FIGS. 3 and 5. The articulation tube 20 is positioned to fit immediately distal the wings 252 of wing nut 250, better seen in FIG. 3, so that motion of wing nut 250 causes motion of tube 20. The drive tube 30 extends through the entire mechanism and is connected at its proximalmost end to the drive ball 310, which is maintained within the trigger 350 contained at the proximal end of the instrument 1. This drive ball 310 is held by set screw 320 into trigger 350.

The trigger 350 is capable of rotating about the handle 360 of the instrument via a pin 330 which connects both the handle and the trigger at pivot holes 352, 362. This pin 330 is held in place by a trigger cover 340 as better seen in FIG. 3. Thus, it will be readily understood that the driving of the end effectors 60, 70 of this instrument is accomplished solely by the scissoring action of the handle 360 with respect to the trigger 350. When the trigger 350 is rotated so that it is closer to the handle 360, the drive ball 310 is caused to pivot proximally with respect to the handle 360. This proximal motion of the drive ball 310 causes proximal motion of drive rod 30, and consequently causes a closing of the end effectors 60, 70 one on the other. Thus, one may accomplish grasping or scissoring, or any other desired endoscopic function. The motion of the trigger 350 away from the handle 360 causes pivoting about pin 330 so that there is caused a distal motion of the drive rod 30. In this way, this causes a distal motion at the distal end 32 of the drive rod 30, causing the end effector jaws 60, 70 to move away from one another, and therefore accomplish opening of a scissors or graspers or any other endoscopic end effectors.

This driving capability of the mechanism 1 must now be understood in conjunction with the articulation or angulation described above, taken further in conjunction with rotation of this instrument. First, the articulation aspects of this instrument will be described. Articulation is accomplished by the articulation knob assembly, which comprises the end cap 240, the front articulation knob 260 and the rear articulation knob 270. Held within this articulation knob assembly is an articulation wing nut 250, fitted within slot 164 of the double slotted tube 160. Slotted tube 160 is screwed at threads 162 to cap 240. This mechanism is arranged so that the double slotted tube 160 holds the articulation wing nut 250 assembly securely. A spring 230 regulates motion of the articulation wing nut 250 between end cap 240 and slot 164. This articulation wing nut 250 is in turn connected to the articulation drive tube 20, which allows it to interact with the end effectors 60, 70 and clevis 40 at of the distal end of the mechanism. Of course, because the outer tube 10 is also connected at flange 14 to the articulation end cap 240, when articulation is accomplished, the articulation tube 20 is capable of moving with respect to the outer tube 10.

When it is desired to perform articulation, the user rotates the articulation knob assembly. In this way, the inner helical threads 262 of the front articulation knob 260 cause a relative motion between wings 252 of the articulation wing nut 250 and the remainder of the instrument. In other words, with a counterclockwise motion, the articulation wing nut 250 is pulled proximally toward the user within the center 264 of knob 260. In this way, the articulation tube 20 similarly moves proximally, and therefore sliding elbow 120 is also moved proximally. This tends to straighten the clevis 40 with respect to the longitudinal axis of the shaft of the mechanism. Conversely, when the knobs 260, 270 are moved clockwise, the helical portion 262 of knob 260 causes the articulating wing nut 250 to move distally within slot 164. This distal motion causes distal motion of the slider elbow 120, and in turn causes angulation of the clevis 40 with respect to the longitudinal axis of the shaft.

Helix 262 converts the rotary motion of the knobs 260, 270 into linear motion of the articulation tube 20. This rotary motion gives a generally one-to-one ratio between motion and articulation. Thus, roughly 120° of knob rotation is needed for 90° of shaft articulation. Thus, the user is able to get a general "feel" for angulation of clevis 40 over a relatively easy (from the user's perspective) length of motion.

Next, it will be necessary to describe rotational motion of this instrument. However, in order to do so, it will first be necessary to understand the interrelationship between the articulation portion of the instrument and the rotational portion of the instrument. Generally, as can be seen from the figures, rotation spring 220 causes the rotation knob 290 to be moved proximally within the instrument. This rotation knob 290 has contained within it a series of locking ratchets 292. These locking ratchets 292 mate with the ratchets 302 of rotational lock 300. The rotational lock 300 is contained in opening 364 in the handle 360 and is maintained therein in a fixed position by retaining ring 200 placed over distal end 182 of tube 180, over which lock 300 is held. Thus, when the rotation spring 220 pushes on the rotation knob, it causes the flanges on the rotation knob 290 to mate with the rotation lock ratchets 302, so that the rotation knob 290 is statically placed within the handle 360. Thus, typically when the user rotates articulation knobs 260, 270, these articulation knobs 260, 270 are able to be rotated independent of rotation of the rotation knob 290. This causes motion of the articulation wing 250 and its concomitant articulation tube 20 with respect to the entire mechanism, including the stationary outer tube 10 and the stationary handle 360, trigger 350 and rotation knob 290 assembly contained therein.

Held within the distal opening 294 of rotation knob 290 is articulation ratchet lock 280. This articulation ratchet lock 280 contains a series of knurls 282 which are capable of interacting with the knurls 272 contained in the proximal portion 274 of the rear articulation knob 270. Further held within the center of rotation knob 290 is tube 180. This tube 180 is fixedly placed within fixed handle 360. It is held therein by retaining ring 200. It will be noticed that the tube 180 has attached to it a flange 182 upon which is held the rotation lock 300, as above described. The rotation lock 300 is held between the flange 182 and the retaining ring 200. The tube 180 has threads 184 on its distal end which are matedly threaded within the threads of the slotted tube 160 held within the articulating knobs 260, 270. Thus, the articulating knobs 260, 270 are free to rotate about the handle 360 and therefore, the articulation wing 250 moves with respect to the handle 360/trigger 350 combination. The drive tube 30 is extended through the center 186 of the approximately 10 mm tube 180 and into the handle 360 as previously described.

An articulation spring 210 is placed between articulation ratchet lock 280 and spring retainer 170 which is held in place by snap ring 190 on slotted tube 160. This assembly is placed within distal opening 294 of the rotation knob on the proximal side of the articulation ratchet lock 280. Thus, the rotation spring 220 is able to place a distal force on the articulation ratchet lock 280. However, because this rotation spring 220 has a lower spring force than the more stiffer articulation spring 210, the free floating articulation ratchet lock 280 is generally placed in a position proximally displaced from the rear articulation knob 270. Thus, the rotation spring 220 also places a proximal force on the rotation knob 290 so that knob 290 is engaged with the rotation ratchet lock 300. The articulation spring 210 is held in place over distal ends 168 of tube 160 by spring retainer 170 held over slotted tube 160 by retainer rings 190.

When it is desired to rotate the tubes 10, 20, 30 with respect to the handle 360, the user needs to place a distal force on the rotational knob 290. Articulating ratchet lock 280 now contacts the articulation knob 270. Thus, the rotation knob 290 now engages the slotted tube 160 so that slotted tube 160 transmits rotation to helical thread 262 of the front articulation knob 260, which now engage the wings 252 of the articulation wing nut 250 in a rotational sense only, and not longitudinally, so that the articulation tube is also effectively "locked" in place with respect to the longitudinal position of the articulation knobs 260, 270. Thus, the distal motion of the rotation knob 290 causes a "locking-up" of the entire rotational mechanism. In this way, rotation of the rotational knob 290 causes rotation of the articulation knobs 260, 270, which in turn causes rotation of the outer tube 10 as well as the articulation tube 20. This rotation further causes simultaneous rotation of the fixed elbow 130, as well as the clevis 40. Thus, the rotational position of the jaws 60, 70 is now effected.

Because the jaws are connected via the drive cable 50 to the drive rod 30, this causes rotation of the drive rod 30 within the entire mechanism. (Normally, it is to be remembered that the drive rod 30 moves independently of the articulation tube 20 and the outer tube 10.) Rotation of the drive tube 30 causes rotation of the ball 310 within the handle 360. Thus, orientation of the drive rod 30 now is effected within the handle 360. However, as the trigger 350 is able to cause motion of the drive rod 30 at any rotational position of the drive rod 30, utility of the handle 360/trigger 350 combination is not effected.

Of course, as previously explained, there is also the possibility of articulation of the instrument when the articulation knobs 260, 270 are not held in contact with the rotational knob 290.

With all of the functional capabilities of this mechanism now adequately described, this device has been described in connection with a particularly preferred embodiment. It is to be realized that the equivalents of this invention are intended to be covered, and such invention and its equivalents are to be derived from the appended claims.

We claim:

1. An endoscopic mechanism comprising:
   an endoscopic portion containing an outer tube which defines a longitudinal axis of said tube and through which may be operated an drive rod;
   a drive rod contained within said outer tube, said drive rod containing a proximal end connected to a handle, and a distal end connected to an end effector portion;
   a trigger connected to said drive rod said trigger capable of operating said end effector portion; and
   wherein said end effector portion is capable of being angulated up to 90° with said outer tube; and
   wherein said end effector portion is connected to an articulation tube concentric to said outer tube, and said articulation tube capable of moving said end effector portion with respect to said longitudinal axis.

2. The mechanism of claim 1 further including means attached to said handle for rotating said outer tube about said longitudinal axis.

3. The mechanism of claim 1 wherein said drive rod is connected to a drive cable at said end effector portion, said cable capable of operating at any position of said end effector portion.

4. The mechanism of claim 1 wherein said articulation tube is connected in said handle to an articulation knob.

5. The mechanism of claim 4 wherein said end effector portion is capable of rotating about said longitudinal axis.

6. The mechanism of claim 5 wherein said end effector portion is connected to said outer tube, and said outer tube is manipulable within said handle by a rotation knob.

7. The mechanism of claim 6 wherein said rotation knob is matable with said articulation knob, such that said rotation knob is capable of rotating said outer tube only when said outer tube is in contact with said articulation knob.

8. A mechanism for performing endoscopic procedures comprising:
   an outer tube having a hollow interior and defining a longitudinal axis;
   an end effector portion connected to said hollow outer tube, said end effector portion pivotable about said tube;
   an articulation mechanism connected to said end effector portion, said articulation mechanism reciprocable with respect to said longitudinal axis;
   and a handle portion attached to said articulation mechanism, said handle portion containing an articulation knob capable of reciprocating said articulation tube; and
   wherein said articulation knob contains a helical interior, and said articulation tube is connected to a winged nut within said helical interior, such that rotation of said articulation knob causes said winged nut to reciprocate said articulation tube with respect to said longitudinal axis.

9. The mechanism of claim 8 wherein said articulation knob is capable of causing said end effector portion of pivoting up to 90° about said outer tube.

10. The handle of an endoscopic instrument containing a shaft and wherein said handle is connected to one knob capable of causing said instrument to perform one function, and a second knob capable of causing said instrument of performing a second function, said handle further containing a spring mechanism separating said knobs; and
   wherein said second knob requires a force to be applied by the user to overcome the spring force of said spring force causes engagement of said first knob and said second knob and said engagement of said knobs allows said second knob to cause said second function.

11. The handle of claim 10 wherein said engagement prevents said first knob to cause said first function.

12. The handle of claim 10 wherein said first knob is an articulation knob, and said first function is articulation of said instrument shaft.

13. The handle of claim 10 wherein said second knob is a rotational knob, and said second function is rotation of said shaft.

14. The handle of claim 10 wherein said knobs each contain knurls which interengage one another during said engagement.

15. The handle of claim 10 wherein said second knob is rigid by said spring force to a locked portion with said handle when said knobs are not engaged.

* * * * *